United States Patent [19]
Sipe

[11] 3,974,491
[45] Aug. 10, 1976

[54] LOAD SIGNALING DEVICE FOR A PATIENT'S FOOT

[75] Inventor: John Joseph Sipe, Philadelphia, Pa.

[73] Assignee: Smithkline Corporation, Philadelphia, Pa.

[22] Filed: July 22, 1974

[21] Appl. No.: 490,313

[52] U.S. Cl. .............................. 340/272; 340/240; 340/279; 200/85 R; 200/86.5; 177/209; 128/2 S; 73/172; 33/3 A
[51] Int. Cl.² .................... G01D 21/04; A61B 5/00; G01M 19/00
[58] Field of Search .................. 340/279, 272, 240; 200/85 R, 86.5; 177/208, 209; 116/70; 128/2 R, 2.1; 73/172; 46/175; 33/3 A

[56] References Cited
UNITED STATES PATENTS

| | | | |
|---|---|---|---|
| 1,824,663 | 9/1931 | Munbrun | 340/273 UX |
| 2,558,805 | 7/1951 | Yaglou | 73/172 |
| 2,972,132 | 2/1961 | Putney | 340/240 |
| 3,305,036 | 2/1967 | Walters | 177/209 |
| 3,699,398 | 10/1972 | Newmeyer | 340/272 X |
| 3,702,999 | 11/1972 | Gradisar | 340/272 |
| 3,791,375 | 2/1974 | Pfeiffer | 177/209 X |

*Primary Examiner*—John W. Caldwell
*Assistant Examiner*—William M. Wannisky
*Attorney, Agent, or Firm*—Smith, Harding, Earley & Follmer

[57] ABSTRACT

A device for signaling a patient when a predetermined load is placed on the patient's foot comprises a resilient foot pad having a toe end and a heel end and adapted to substantially cover the inner sole of a shoe. A resilient liquid filled tube is mounted within the pad with the tube extending from adjacent the toe end to adjacent the heel end of the pad. A signaling device is controlled by a pressure responsive means in communication with the liquid in the tube for the actuation of the signaling means at a predetermined pressure of said liquid.

5 Claims, 6 Drawing Figures

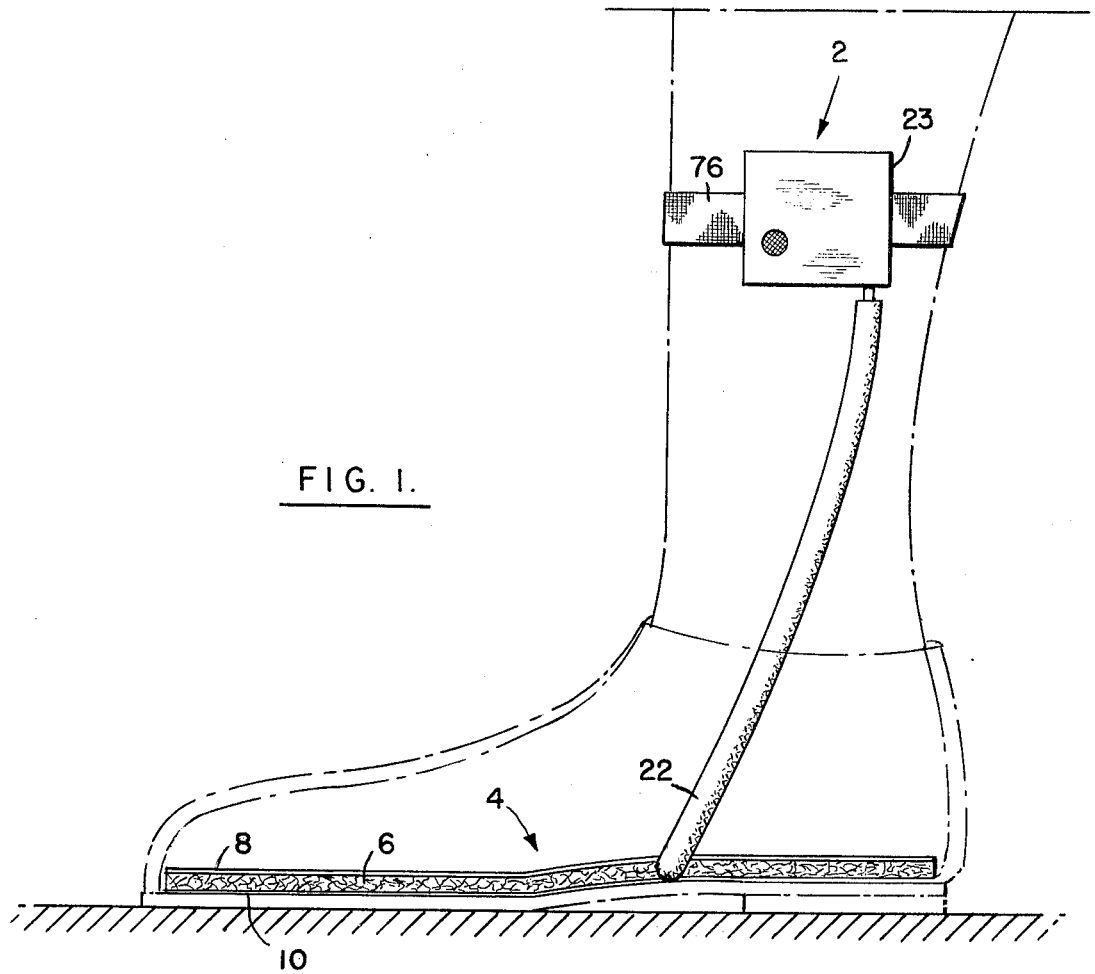
FIG. 1.
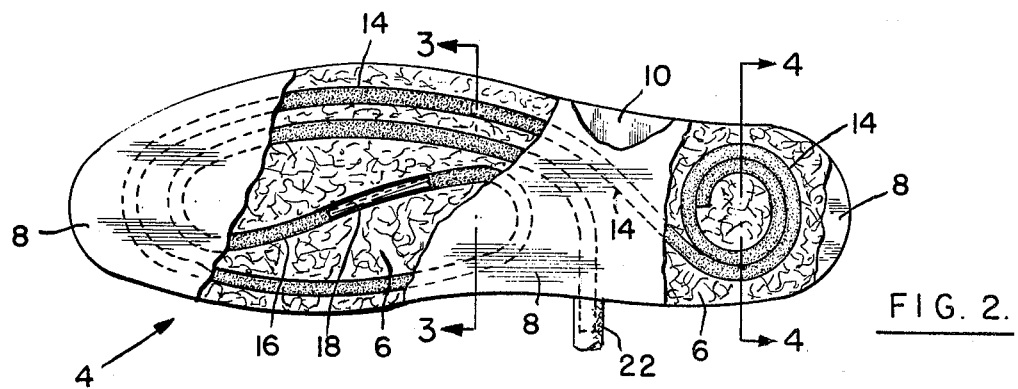
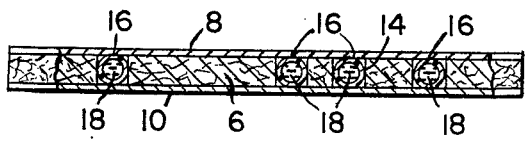
FIG. 3.
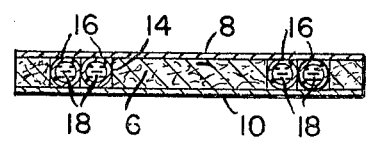
FIG. 4.

LOAD SIGNALING DEVICE FOR A PATIENT'S FOOT

BACKGROUND OF THE INVENTION

Devices for warning the patient when a predetermined load is placed on his foot are known for use in situations where due to a fracture or orthopedic surgery the load on a leg must be limited. Gradisar U.S. Pat. No. 3,702,999 and Pfeiffer U.S. Pat. No. 3,791,375 each disclose such a device. The prior art devices employ a plurality of sensing devices each of which senses the load in a particular location. In an effort to sum the responses of the separate sensing units, Pfeiffer relies upon measuring flow instead of pressure. In accordance with this invention a single unitary sensing device in the form of a liquid filled tube senses the loading under the patient's foot and eliminates the necessity for having a system for summing a plurality of loads. In addition, this invention combines accuracy with low cost and reliability. The device of the invention can be used in either foot interchangeably.

BRIEF SUMMARY OF THE INVENTION

A device for signaling a patient when a predetermined load is placed on the patient's foot comprises a resilient foot pad having a toe end and a heel end and adapted to overlie the inner sole of a shoe. A resilient liquid filled tube is mounted within the pad with the tube extending from adjacent the toe end to adjacent the heel end of the pad. A signaling device is controlled by a pressure responsive means in communication with the liquid in the tube for the actuation of the signaling means at a predetermined pressure of said liquid. Advantageously, the tube has a plurality of loops adjacent both the heel and toe portions. The pressure at which the signaling means is actuated can be varied.

BRIEF DESCRIPTION OF THE DRAWINGS

FIG. 1 is a left side elevation of a device in accordance with the invention;

FIG. 2 is a plan view, partially broken away, of the foot pad portion of the device of FIG. 1;

FIG. 3 is a vertical section taken on the plane indicated by the line 3—3 in FIG. 2;

FIG. 4 is a vertical section taken on the plane indicated by the line 4—4 in FIG. 2;

DETAILED DESCRIPTION

Figure 5:
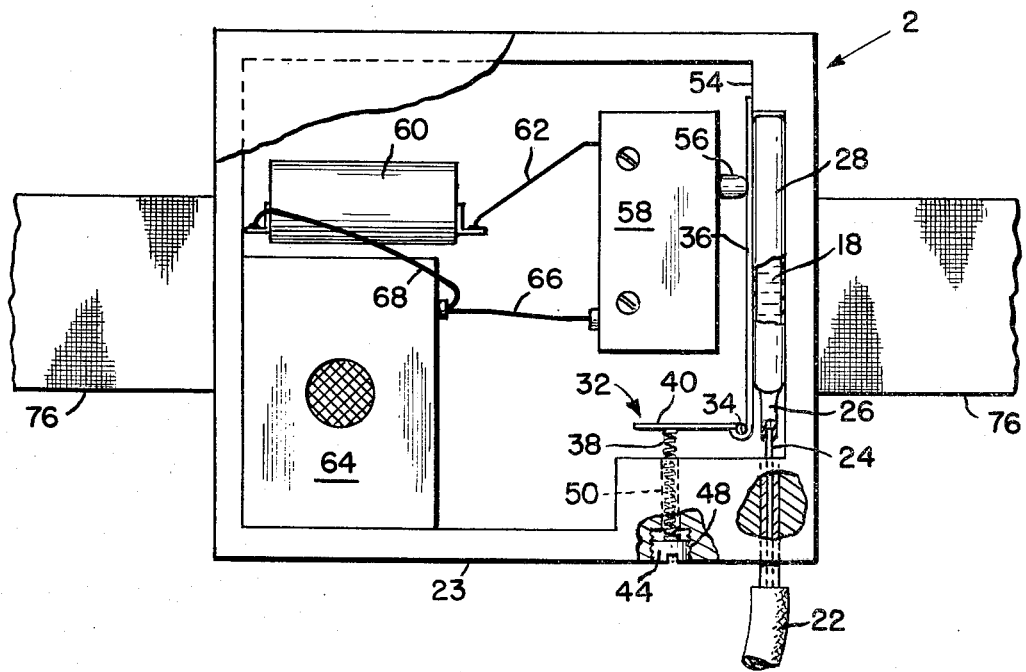
FIG. 5 is an elevational view of the signaling device and a portion of the sensing mechanism of the device of FIG. 1.
Figure 6:
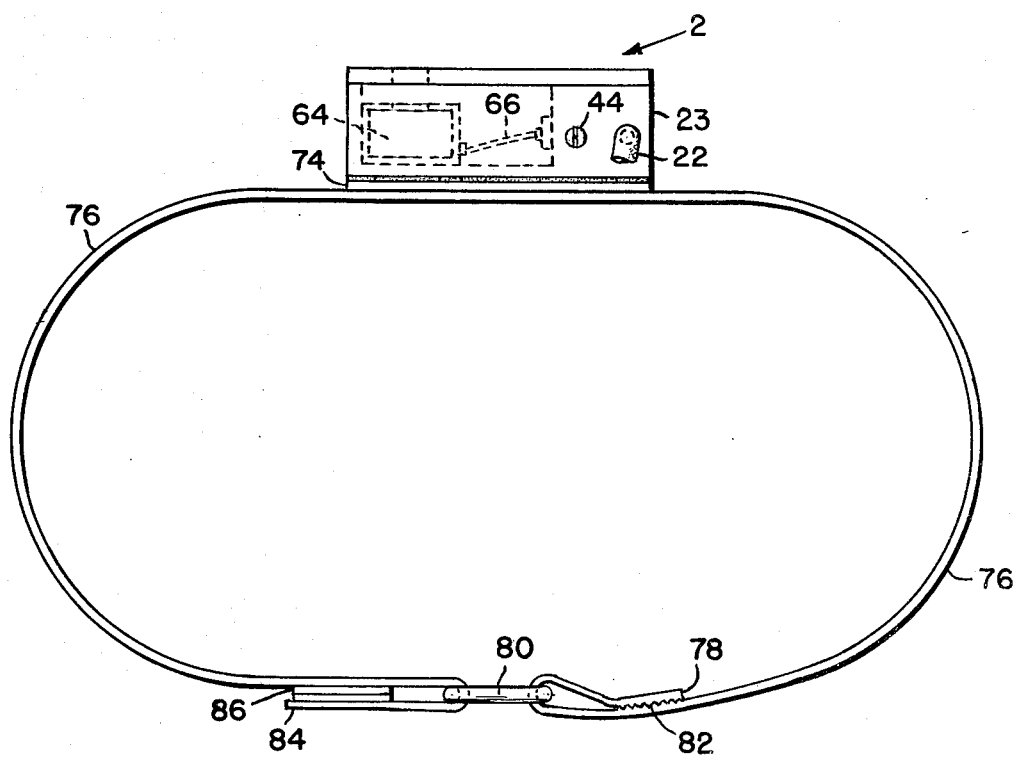
FIG. 6 is a plan view of the structure of FIG. 5 showing the means for securing to a patient's leg.

A device 2 in accordance with the invention has a resilient foot pad 4 having a core of resilient material 6 which may be, for example, sponge rubber or a foamed plastic such as, for example: foamed polyurethane or foamed ethylene-propylene diene. Core 6 is adhesively secured to sheets 8 and 10 of, for example, leather, a rubber coated fabric, canvas or plastic such as, for example: a vinyl resin, for example, polyvinyl chloride. Core 6 is cut out as indicated at 14 to provide for space for the reception of a resilient tube 16 which is filled with a liquid 18 such as water. Sheets 8 and 10 are in contact with tube 16. A marked advantage of the pad 4 is that it can be placed in a shoe for the right foot as illustrated in FIG. 1, or it can be turned upside down and placed in a shoe for the left foot.

Tube 16 is connected to a tube 22 which in turn is connected to a tube connector 24 which is mounted in box 23 and is received inside the neck 26 of a resilient bladder 28 of, for example, rubber. A bell crank lever 32 is pivotally mounted in box 23 as shown at 34 and has an arm 36 biased against bladder 28 by a compression coil spring 38 which has one end abutting against arm 40 of bell crank 32 and the other end against a plug 44 threadably engaging box 23 at 48. Spring 38 freely passes through an opening 50 in box 23. Box 23 has a shoulder 54 which acts as a stop for arm 36. Arm 36 engages a control button 56 of a switch 58. One side of switch 58 is wired to a battery 60 as indicated at 62, and the other side is wired to one side of a buzzer 64 as indicated at 66. The other side of buzzer 64 is wired to battery 60 as indicated at 68.

Box 23 is adhesively secured to a hook sheet 74 which in turn is secured to a loop band 76. Sheet 74 and band 76 form a hook and loop fastener of the type sold under the trademark Velcro. Band 76 has one end 78 passed through a metal ring 80 and stitched back against itself as indicated at 82. The other end 84 is passed through ring 80 and has adhesively secured thereto a hook strip 86 for cooperation with loop band 76 to removably secure end 84 back against the band 76.

OPERATION

Prior to use, plug 44 is adjusted so that a predetermined desired pressure in bladder 28 will actuate switch 58. Pad 4 is then placed in the patient's shoe, slipper or the like and band 76 tightened and secured on the patient's leg. Box 23 is then secured to the band. As the patient increases the weight on his foot the pressure of the liquid inside tube 16 is increased, the major resistance to the compression of pad 4 being provided by the resilient core 6. Nonetheless, pressure is proportionally exerted on tube 16 which in turn increases the pressure of liquid 18 within the tube 16 and bladder 28 which tends to urge bell crank 36 to rotate counterclockwise as viewed in FIG. 5 against the force exerted by compression coil spring 38. When the pressure of the liquid within bladder 28 overcomes the force exerted by spring 38, operating plunger 56 is depressed actuating switch 58 which in turn actuates buzzer 64 signaling the patient that the predetermined weight has been placed on his foot. Irrespective of the distribution of the load on the foot, the pressure of the fluid in bladder 28 will be proportional to the total load since the volumetric compression of the tube 16 is proportional to the volumetric compression of the core 6 which in turn is proportional to the load irrespective of where the load is applied or how the load is distributed on the pad 4.

I claim:

1. A device for signaling a patient when a predetermined load is placed on the patient's foot comprising:
    a resilient foot pad having a toe end and a heel end and adapted to overlie the inner sole of a shoe.
    a resilient tube mounted within said pad, said tube extending from adjacent the toe end of the pad to adjacent the heel end of the pad,
    a liquid filling said tube,
    signaling means, pressure responsive means in communication with the liquid in said tube to control the actuation of said signaling means at a predetermined pressure of said liquid.

2. The device of claim 1 in which the tube has a plurality of loops within the foot pad.

3. The device of claim 1 in which the pressure responsive means includes a resilient expansible member and a switch actuated by said member.

4. The device of claim 3 in which the expansible member is a bladder.

5. The device of claim 1 having adjustable means to vary the pressure at which the signaling means is actuated.

* * * * *